(12) United States Patent
Csákai et al.

(10) Patent No.: US 7,550,457 B2
(45) Date of Patent: Jun. 23, 2009

(54) PHARMACEUTICALLY EFFECTIVE COMPOUNDS

(75) Inventors: Zita Jegesné Csákai, Vilonya (HU); Ede Márványos, Budapest (HU); László Ürögdi, Budapest (HU); Magdolna Bathóné Török, Balatonfured (HU); László Dénes, Budapest (HU)

(73) Assignee: CytRx Corporation, Los Angeles, CA (US)

( * ) Notice: Subject to any disclaimer, the term of this patent is extended or adjusted under 35 U.S.C. 154(b) by 0 days.

(21) Appl. No.: 11/981,422

(22) Filed: Oct. 30, 2007

(65) Prior Publication Data

US 2008/0058323 A1 Mar. 6, 2008

Related U.S. Application Data

(60) Division of application No. 10/889,966, filed on Jul. 12, 2004, now Pat. No. 7,361,655, which is a continuation-in-part of application No. PCT/HU03/00003, filed on Jan. 10, 2003.

(30) Foreign Application Priority Data

Jan. 11, 2002 (HU) .................... 0200109
Dec. 17, 2002 (HU) .................... 0204362

(51) Int. Cl.
*A61K 31/535* (2006.01)
(52) U.S. Cl. ............... 514/222.5; 514/229.2; 544/66
(58) Field of Classification Search ........... 514/222.5
See application file for complete search history.

(56) References Cited

U.S. PATENT DOCUMENTS

| | | | |
|---|---|---|---|
| 4,187,220 A | 2/1980 | Takacs et al. |
| 4,404,384 A | 9/1983 | Gebert et al. |
| 4,451,286 A | 5/1984 | Martin et al. |
| 5,147,879 A | 9/1992 | Nagy et al. |
| 5,239,077 A | 8/1993 | Bertok et al. |
| 5,278,309 A | 1/1994 | Bertok et al. |
| 5,296,606 A | 3/1994 | Nagy et al. |
| 5,328,906 A | 7/1994 | Nagy et al. |
| 5,334,600 A | 8/1994 | Van Duzer et al. |
| 5,919,796 A | 7/1999 | Barabas et al. |
| 6,649,628 B1 | 11/2003 | Kurthy et al. |
| 6,653,326 B1 | 11/2003 | Vigh et al. |
| 7,126,002 B2 | 10/2006 | Urogdi et al. |
| 7,148,239 B2 | 12/2006 | Vigh et al. |

FOREIGN PATENT DOCUMENTS

| | | |
|---|---|---|
| CA | 2059184 | 7/1992 |
| EP | 0369944 | 5/1990 |
| GB | 1540028 | 2/1979 |
| GB | 1582029 | 12/1980 |
| WO | WO 90/04584 | 5/1990 |
| WO | WO 90/08131 | 7/1990 |
| WO | WO 92/03130 | 3/1992 |
| WO | WO 95/30649 | 11/1995 |
| WO | WO 97/00251 | 1/1997 |
| WO | WO 97/13504 | 4/1997 |
| WO | WO 97/16439 | 5/1997 |
| WO | WO 98/06400 | 2/1998 |
| WO | WO 98/43948 | 10/1998 |
| WO | WO 98/47362 | 10/1998 |
| WO | WO 00/35914 | 6/2000 |
| WO | WO 00/50403 | 8/2000 |
| WO | WO 01/79174 | 10/2001 |
| WO | WO 2005/041965 | 5/2005 |

OTHER PUBLICATIONS

Chalmers (TiPS vol. 17, pp. 166-172 Apr. 1996).*
Beltrao et al., "Preparation and Spectral Study of O-methyl=benzamidoximes," *Chemical Abstracts*, 89:215038s (1978).
Burger, "Pro-Drugs," *A Guide to the Chemical Basis of Drug Design*, p. 15, 1.3.1 (1983).
Chalmers et al., "Corticotrophin-releasing factor receptors: from molecular biology to drug design", *TIPS*, 17:166-172 (1996).
Dekoning, et al., "Org. 2766 improves Functional and Electrophysical Aspects of Regenerating Sciatic Nerve in the Rat," *Peptides*, 8(3):415-422 (1987).
Morrison, et al., *Organic Chemistry*, Allyn and Bacon, Inc. (Boston), 205-211, (1983).
Showa Denko K.K., "Insecticidal (hydroxyimino) butanones,", *Chemical Abstracts*, 102:220443m (1985).
Sorensen et at., "Soluble expression of recombinant proteins in the cytoplasm of *Escherichia coli*," *Microbial Cell Factories*, 4:1-8(2005).
Stanley, "Sensory and Motor Nerve Conduction Velocities and the Latency of the H-Reflex During Growth of the Rat," *Experimental Neurology*, 71(2):497-506 (1981).

(Continued)

*Primary Examiner*—Kahsay T Habte
(74) *Attorney, Agent, or Firm*—Ropes & Gray LLP; Barbara A. Ruskin; Carl A. Morales

(57) ABSTRACT

The subject invention relates to carboxamidine derivatives, to pharmaceutical compositions containing the carboxamidine derivatives of the invention, and the use thereof for the treatment of vascular diseases and in the preparation of pharmaceutical compositions for the treatment of vascular diseases.

19 Claims, No Drawings

OTHER PUBLICATIONS

Tesfamariam, et al., "Contraction of Diabetic Rabbit Aorta Caused by Endothelium-Derived $PGH_2$-$TxA_2$," *American Journal of Physiology*, 257(5):1327-1333 (1989).

Winslow, et al., "Comparative Effects of the Isomers of Bepridil on Isolated Coronary and Aortic Arteries," *European Journal of Pharmacology*, 166(2):241-249 (1989).

\* cited by examiner

US 7,550,457 B2

PHARMACEUTICALLY EFFECTIVE COMPOUNDS

CROSS REFERENCE TO RELATED APPLICATIONS

This application is a divisional of U.S. application Ser. No. 10/889,966, filed Jul. 12, 2004, now U.S. Pat. No. 7,361,655 which is a continuation-in-part of International patent application No. PCT/HU03/00003, filed Jan. 10, 2003.

DETAILED DESCRIPTION OF THE INVENTION

The invention relates to pharmaceutically effective hydroxylamine derivatives, which are useful in the treatment of vascular diseases.

The invention relates to the use of compounds of general formulae (I), (II) and (III)

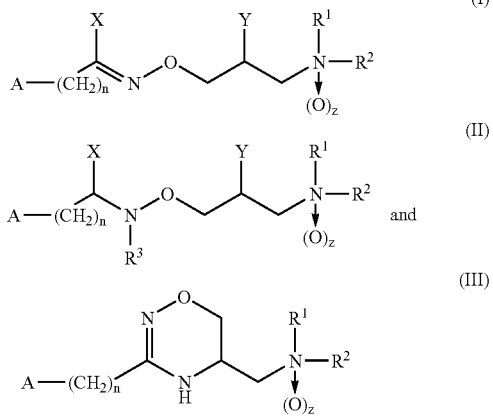

$R^1$ and $R^2$ independently represent a hydrogen atom or a straight or branched $C_{1-6}$ alkyl group optionally substituted with a phenyl group, or $R^1$ and $R^2$ together with the nitrogen atom attached thereto form a 5-7 membered saturated heterocyclic ring optionally containing further nitrogen and/or oxygen heteroatoms, which heterocyclic ring is optionally substituted with one or more hydroxy, oxo or benzyl groups, A represents a phenyl group optionally substituted with one or more $C_{1-4}$ alkyl, $C_{1-4}$ haloalkyl or nitro groups or halogen atoms, or a 5-6 membered heteroaromatic ring containing one or more nitrogen, oxygen or sulfur heteroatoms, optionally having N-oxide structure on the nitrogen heteroatom, n is zero, 1 or 2, n is zero or 1, in compounds of general formulae (I), X represents a halogen atom or —$NR^4R^5$ group, where $R^4$ and $R^5$ independently represent a hydrogen atom or a straight or branched $C_{1-6}$ alkyl group, in compounds of general formulae (II), X refers to oxygen atom, $R^3$ represents a hydrogen atom or a straight or branched $C_{1-6}$ alkyl group, Y represents a hydrogen atom or hydroxy group, halogen atom or $C_{1-22}$ acyloxy group, with the restriction that if $R^4$ and $R^5$ are simultaneously hydrogen atoms, Y is other than hydroxy group, with the proviso that in compounds of general formulae (I) and (II) where Y is other than halogen, a) $R^1$ and $R^2$ together with the nitrogen atom attached thereto form a 5-7 membered, saturated heterocyclic ring optionally containing further nitrogen and/or oxygen heteroatom, which heterocyclic ring is substituted with one or more hydroxy, oxo or benzyl groups and/or b) A is an N-containing heteroaromatic ring, which has N-oxide structure on the nitrogen heteroatom, and/or c) z is 1, with the further proviso that if X is halo and Y is hydroxy or acyloxy in compounds of general formulae (I), $R^1$ and $R^2$ together with the nitrogen atom attached thereto form a 5-7 membered, saturated heterocyclic ring optionally containing further nitrogen and/or oxygen heteroatom, which heterocyclic ring is substituted with one or more hydroxy, oxo or benzyl groups and with the proviso for compounds of general formulae (III) that if $R^1$ and $R^2$ independently represent a hydrogen atom or a straight or branched $C_{1-6}$ alkyl group optionally substituted with a phenyl group, or together with the nitrogen atom attached thereto form a 5-7 membered saturated heterocyclic ring optionally containing further nitrogen and/or oxygen heteroatoms, then A is a heteroaromatic ring containing oxygen or sulfur heteroatom or an N-containing heteroaromatic ring having N-oxide structure on the nitrogen heteroatom and if A is a phenyl group optionally substituted with one or more $C_{1-4}$ alkyl, $C_{1-4}$ haloalkyl or nitro groups or halogen atoms, or a 5-6 membered N-containing heteroaromatic ring, then $R^1$ and $R^2$ together with the nitrogen atom attached thereto form a 5-7 membered, saturated heterocyclic ring optionally containing further nitrogen and/or oxygen heteroatom, which heterocyclic ring is substituted with one or more hydroxy, oxo or benzyl groups, and of the salts and optically active forms of the above compounds for the production of pharmaceutical products used in the treatment and/or prevention of vascular diseases or diseases related to vascular disorders.

Compounds of similar structure are known from WO 97/16439. These compounds increase molecular chaperon expression, or molecular chaperon activity in cell exposed to a physiological stress. Due to this characteristic, they are useful for the treatment of diseases connected with the functioning of the chaperon system.

The protective and regenerating effect that compounds of similar structures have for vascular endothelial cells is known from WO 98/06400. These compounds are primarily useful for the prevention of damage caused by ischemia and for the treatment of cardiovascular and cerebrovascular diseases.

We have found that when the hydroxylamine derivatives described in the cited literature are chemically modified, preferably in such a way that, according to general formulae (I), (II) and (III) above, 1) a halogen atom is introduced into the propylene group of the aminopropyl group connected to the hydroxylamine part as substituent and/or 2) N-oxide is formed on the nitrogen atoms in the terminal groups of the molecule, namely on the nitrogen atom connected to the propylene group of the above mentioned aminopropyl group and/or on the nitrogen atom located in the heteroaromatic ring of the molecule, then the resulting products are hydroxylamine derivatives which possess much more favorable pharmacological properties against vascular illnesses than known compounds which have been found to be useful for this purpose. Namely, the effect of these compounds is more intensive than that of the known prior art compounds used for similar purposes. Therefore they are especially useful as active ingredients in the treatment or prevention of vascular diseases or diseases associated with vascular disorders.

Based on this observation, this invention relates to the use of compounds of general formulae (I), (II) and (III)—where $R^1, R^2, R^3, A, X, Y$, n and z are as above -, and to the use of the salts and optically active forms of the above compounds for the production of pharmaceutical products for the treatment and/or prevention of vascular diseases or diseases associated with vascular disorders.

A considerable part of compounds of general formulae (I), (II) and (III) are novel compounds.

Novel compounds are compounds of general formulae (I) wherein $R^1$ and $R^2$ independently represent a hydrogen atom or a straight or branched $C_{1-6}$ alkyl group optionally substituted with a phenyl group, or $R^1$ and $R^2$ together with the nitrogen atom attached thereto form a 5-7 membered saturated heterocyclic ring optionally containing further nitrogen and/or oxygen heteroatoms, which heterocyclic ring is optionally substituted with one or more hydroxy, oxo or benzyl groups, A represents a phenyl group optionally substituted with one or more $C_{1-4}$ alkyl, $C_{1-4}$ haloalkyl or nitro groups or halogen atoms, or a 5-6 membered heteroaromatic ring containing one or more nitrogen, oxygen or sulfur heteroatoms, optionally having N-oxide structure on the nitrogen heteroatom, n is zero, 1 or 2, z is zero or 1, X represents a halogen atom or —$NR^4R^5$ group, where $R^4$ and $R^5$ independently represent a hydrogen atom or a straight or branched $C_{1-6}$ alkyl group, Y represents a hydrogen atom or hydroxy group, halogen atom or $C_{1-22}$ acyloxy group, with the restriction that if $R^4$ and $R^5$ are simultaneously hydrogen atoms, then Y is other than hydroxy group, with the proviso that a) if Y is hydrogen and/or X is a —$NR^4R^5$ group, where $R^4$ and $R^5$ have the above meanings, $R^1$ and $R^2$ together with the nitrogen atom attached thereto form a 5-7 membered, saturated heterocyclic ring optionally containing further nitrogen and/or oxygen heteroatom, which heterocyclic ring is substituted with one or more hydroxy, oxo or benzyl groups and/or A is an N-containing heteroaromatic ring, which has N-oxide structure on the nitrogen heteroatom, or b) if X is halo and Y is hydroxy or acyloxy, $R^1$ and $R^2$ together with the nitrogen atom attached thereto form a 5-7 5 membered, saturated heterocyclic ring optionally containing further nitrogen and/or oxygen heteroatom, which heterocyclic ring is substituted with one or more hydroxy, oxo or benzyl groups, and the stereoisomers of the above compounds and their salts.

Novel compounds are compounds of general formulae (II) wherein $R^1$ and $R^2$ independently represent a hydrogen atom or a straight or branched $C_{1-6}$ alkyl group optionally substituted with a phenyl group, or $R^1$ and $R^2$ together with the nitrogen atom attached thereto form a 5-7 membered saturated heterocyclic ring optionally containing further nitrogen and/or oxygen heteroatoms, which heterocyclic ring is optionally substituted with one or more hydroxy, oxo or benzyl groups, A represents a phenyl group optionally substituted with one or more $C_{1-4}$ alkyl, $C_{1-4}$ haloalkyl or nitro groups or halogen atoms, or a 5-6 membered heteroaromatic ring containing one or more nitrogen, oxygen or sulfur heteroatoms, optionally having N-oxide structure on the nitrogen heteroatom, n is zero, 1 or 2, z is zero or 1, X represents an oxygen atom, $R^3$ represents a hydrogen atom or a straight or branched $C_{1-6}$ alkyl group, Y represents a hydrogen atom or hydroxy group, halogen atom or $C_{1-22}$ acyloxy group, with the proviso that if Y is other than halo, $R^1$ and $R^2$ together with the nitrogen atom attached thereto form a 5-7 membered, saturated heterocyclic ring optionally containing further nitrogen and/or oxygen heteroatom, which heterocyclic ring is substituted with one or more hydroxy, oxo or benzyl groups and/or A is an N-containing heteroaromatic ring, which has N-oxide structure on the nitrogen heteroatom, and the stereoisomers of the above compounds and their salts.

Novel compounds are compounds of general formulae (III) wherein $R^1$ and $R^2$ independently represent a hydrogen atom or a straight or branched $C_{1-6}$ alkyl group optionally substituted with a phenyl group, or $R^1$ and $R^2$ together with the nitrogen atom attached thereto form a 5-7 membered saturated heterocyclic ring optionally containing further nitrogen and/or oxygen heteroatoms, which heterocyclic ring is optionally substituted with one or more hydroxy, oxo or benzyl groups, A represents a phenyl group optionally substituted with one or more $C_{1-4}$ alkyl, $C_{1-4}$ haloalkyl or nitro groups or halogen atoms, or a 5-6 membered heteroaromatic ring containing one or more nitrogen, oxygen or sulfur heteroatoms, optionally having N-oxide structure on the nitrogen heteroatom, n is zero, 1 or 2, z is zero or 1, with the proviso that if $R^1$ and $R^2$ independently represent a hydrogen atom or a straight or branched $C_{1-6}$ alkyl group optionally substituted with a phenyl group, or together with the nitrogen atom attached thereto form a 5-7 membered saturated heterocyclic ring optionally containing further nitrogen and/or oxygen heteroatoms, then A is a heteroaromatic ring containing oxygen or sulfur heteroatom or an N-containing heteroaromatic ring having N-oxide structure on the nitrogen heteroatom and if A is a phenyl group optionally substituted with one or more $C_{1-4}$ alkyl, $C_{1-4}$ haloalkyl or nitro groups or halogen atoms, or a 5-6 membered N-containing heteroaromatic ring, then $R^1$ and $R^2$ together with the nitrogen atom attached thereto form a 5-7 membered, saturated heterocyclic ring optionally containing further nitrogen and/or oxygen heteroatom, which heterocyclic ring is substituted with one or more hydroxy, oxo or benzyl groups, and the stereoisomers of the above compounds and their salts.

The invention relates to the above compounds. The invention further relates to pharmaceutical products that contain as active ingredient compounds of general formulae (I), (II) and (III), or their stereoisomers, or their salts, where $R^1, R^2, R^3, A, X, Y$, n and z are as defined above. The following compounds of the invention are especially preferable:

1. N-[3-(1-piperidinyl)propoxy]-pyridin-1-oxide-3-carboxamidine
2. N-[3-(1-piperidinyl)propoxy]-pyridin-1-oxide-3-carboximidoyl chloride 3. N-[2-hydroxy-3-(1-piperidinyl)propoxy]-N'-n-butyl-pyridin-1-oxide-4-carboxamidine 4. N-[3-(1-oxido-1-piperidinyl)propoxy]-3-nitro-benzimidoyl-chloride dihydrate 5. 2-chloro-N-[3-(4-oxido-4-morpholinyl)propoxy]-benzimidoyl chloride 6. (R,S)-5,6-dihydro-5-[(1-piperidinyl)methyl]-3-(1-oxido-3-pyridyl)-4H-1,2,4-oxadiazine 7. 5,6-dihydro-5-[(4-benzyl-1-piperidinyl)methyl]-3-(3-pyridyl)-4H-1,2,4-oxadiazine 8. (R) or (S)-5,6-dihydro-5-[(2-oxo-1-piperidinyl)methyl]-3-(3-pyridyl)-4H-1,2,4-oxadiazine 9. (+)-5,6-dihydro-5-[(1-piperidinyl)methyl]-3-(1-oxido-3-pyridyl)-4H-1,2,4-oxadiazine 10. (R) or (S)-5,6-dihydro-5-[(1-oxido-1-piperidinyl)methyl]-3-(1-oxido-3-pyridyl)-4H-1,2,4-oxadiazine 11. 5,6-dihydro-5-[(4-hydroxy-1-piperidinyl)methyl]-3-(3-pyridyl)-4H-1,2,4-oxadiazine 12. N-[2-chloro-3-(1-piperidinyl)propoxy]-3-benzimidoyl-chloride hydrochloride 13. N-[2-hydroxy-3-(1-piperidinyl)propoxy]-pyridin-1-oxide-3-carboxamide The biological effects of the compounds of the invention were tested by the following experiments:

Wounding Migration Assay in Endothelial Cell Culture

The effect of the compounds of the invention on the wounded monolayers of human umbilical vein endothelial cells (HUVEC) were studied in a cell culture system (in vitro). After reaching confluence, the HUVEC cells were wounded according to the method of Yamamura et al. (J. Surgical Res. 63, 349-354, 1996). The number of migrated cells were registered using computerized image analysis 24 hours after wounding in the absence and presence of the active agents under testing in a concentration of $10^{-6}$ M. The active ingredient described in publication no. WO 98/06400, namely 5,6-dihydro-5-(1-piperidinyl)-methyl-3-(3-pyridyl)-4H-1,2,4-oxadiazine was used as reference compound. The obtained results are given in Table 1.

TABLE 1

| No. of the compound | cell/mm² 24 hours |
|---|---|
| Reference | 30 |
| 4 | 45 |
| 8 | 48 |
| 9 | 52 |
| 11 | 51 |
| 12 | 60 |
| 13 | 54 |

In the following, we give the results of the test of blood vessel relaxing effect, performed in vitro on rat vessels, and also the morphological results of the thoracic aorta.

Three-month-old, genetically hypertonic (SH) Wistar Okamoto rats were treated for one month with various test compounds. Thereafter the functional and morphological tests were performed.

The Vaso-relaxing Effect of the Compounds of the Invention on the Thoracic Aorta of SH Rats (In Vitro Testing)

The test was performed by the method known from the literature [Japan J. Pharmacol., 59, 339-347 (1992)]. The SH rats were anesthetized with Nembutal (40 mg/kg, i. p.), then the thoracic aorta was removed and placed in oxygenized (95% $O_2$+5% $CO_2$) Krebs-Henseleit solution. The composition of the solution (mM): NaCl 118, KCl 4, 7, $CaCl_2$ 2,52, $MgSO_4$ 1,64, $NaHCO_3$ 24,88, $KH_2PO_4$ 1,18, glucose 5,5. The 3-mm-long aorta rings were suspended in a 20 ml organ bath of 37° C. The resting tension was 1 g, which was maintained throughout the equilibration. During the 1 hour equilibration, the medium was changed in every 20 minutes. The vessels were contracted with $10^{-6}$ M methoxamine (approximately 80% of maximal contraction). After reaching the maximal contraction, we tested the vasodilation resulting as the effect of the acetylcholine (Ach) ($10^{-6}$–$10^{-4}$ M), which informed us about the condition of the endothelium of the vessel wall. The contraction force was measured by an isometric strain gauge (SG-01D, Experimentia Ltd), and was registered on an OH-850 polygraph (Radelkis). At this time again, 5,6-dihydro-5-(1-piperidinyl)-methyl-3-(3-pyridyl)-4H-1,2,4-oxadiazine as described in WO 98/06400 was used as a reference compound. The results of these tests are summarized in Table 2.

TABLE 2

The vessel relaxing effect of the compounds of the invention on the thoracic aorta of SH rats (in vitro testing).

| Materials | Ach doses (M) | | |
|---|---|---|---|
| Doses | $10^{-6}$ | $10^{-5}$ | $10^{-4}$ |
| SH control<br>N = 10 | 55.1 | 57.2 | 72.0 |
| Reference<br>n = 12; 20 mg/kg | 77.4 | 80.2 | 81.7 |
| Compound no. 4<br>n = 11; 5 mg/kg | 82.5 | 84.9 | 88.1 |
| Compound no. 8<br>n = 11; 20 mg/kg | 80.3 | 88.0 | 89.2 |
| Compound no. 9<br>n = 10; 5 mg/kg | 87.0 | 87.9 | 93.2 |
| Compound no. 11<br>n = 12; 10 mg/kg | 79.7 | 85.1 | 86.0 |
| Compound no. 12<br>n = 12; 20 mg/kg | 82.3 | 83.5 | 80.4 |
| Compound no. 13<br>n = 10 | 88.4 | 90.3 | 95.2 |

As the table shows, we registered a 30% relaxation decrease in the case of untreated hypertonic animals, which is the result of hypertonia-induced endothelial damage. The test compounds improved the relaxation properties of the vessels significantly, which is the result of the improved functioning of the endothelium, due to the relative increase of the endothelium-related relaxation factors.

Morphological Testing of the Thoracic Aortas with Electron Microscopy

The test was performed according to the procedure known from the literature (Br. J. of Pharmacol., 1995; 115, 415-420). 1 mm² pieces of the aorta wall was cut out of the thoracic aorta of the rats, and were then fixed with 2.5% glutaraldehyde at room temperature for 2 hours. This was followed by a post-fixation with 1% osmium tetroxide for 1 hour. Afterwards, the tissue pieces were dehydrated with ethanol, and embedded in Durcupan ACM. The samples were evaluated qualitatively based on the images recorded on a Hitachi 7100 electron microscope. The results of the test are given in Table 3.

TABLE 3

Electron microscopic examination of the compounds of the invention on the thoracic aorta of SH rats (morphological testing)

| Materials Doses | Degree of regeneration |
|---|---|
| SH control, physiological saline solution | 1 |
| Compound no. 4., 20 mg/kg p. o. | 5 |
| Compound no. 8., 5 mg/kg p. o. | 5 |
| Compound no. 9., 5 mg/kg p. o. | 5 |
| Compound no. 11., 10 mg/kg p. o. | 4 |
| Compound no. 12., 20 mg/kg p. o. | 3 |
| Compound no. 13., 20 mg/kg p. o. | 4 |

The results of the morphological test are expressed on a scale of 1 to 5, depending upon the degree to which the treatment with various test compounds restored the hypertonia-induced endothelium damage, that is, upon the degree of regeneration activity observed. On the scale, 1 was used to refer to cases where no regeneration was observable, 2 refers to weak, 3 to average, 4 to good, and 5 to strong regeneration.

When comparing it to the untreated control, significant protective and regenerative effect was observed after treatment with the compounds of the invention. Due to the treatment, a thin, freshly formed layer covered the wounded subendothelium, which contained cells with active nuclei and rich cytoplasm. Regeneration was shown to be very effective in the case of the majority of the tested molecules.

Compounds of general formulae (I) where Y is a halogen atom are prepared by halogenating the suitable compound containing a hydroxyl group as Y substituent. The other compounds of the invention are prepared by the known method, according to the procedures given in WO 97/16439 and WO 98/06400. Methods for the preparation of certain compounds are demonstrated in the examples.

The subject invention also concerns methods for treating or preventing vascular diseases or diseases related to vascular disorders comprising administering an effective amount of a compound or pharmaceutical composition of the invention to a patient in need thereof.

The compositions of the invention can be made in solid or liquid forms generally used in human and veterinary therapy. For oral administration tablets, coated tablets, dragées, granules, capsules, solutions or syrups, for rectal administration suppositories, and for parenteral administration lyophylised or not lyophylised injections or infusion solutions can be prepared by known preparation methods. The oral compositions may contain fillers such as microcrystalline cellulose, starch, lactose, lubricants, such as stearic acid and magnesium stearate, coating materials such as sugar, film materials such as hydroxymethyl cellulose, flavors or sweeteners such as methyl paraben or saccharine, and colorants. Auxiliaries in the suppositories may be for example cocoa butter and polyethylene glycol. The compositions for parenteral use may contain saline or optional dispersing and wetting agents such as propylene glycol along with the active ingredient.

The dose of the compounds of the invention depends on the illness of the patient and the disease and varies from 0.1 to 200 mg/kg/day, preferably from 0.1 to 50 mg/kg/day. For human therapy, the preferable oral dose is 10-200 mg, in case of rectal administration 1-15 mg, and in case of parenteral treatment 2-20 mg daily for adults. These doses are applied in unit dosage forms optionally distributed to 2-3 administrations, particularly in case of oral treatment.

All patents, patent applications, provisional applications, and publications referred to or cited herein, including Hungarian application Serial Nos. P0200109 and P0204362, are incorporated by reference in their entirety, including all figures and tables, to the extent they are not inconsistent with the explicit teachings of this specification.

The invention is demonstrated by the examples below. These examples should not be construed as limiting. All percentages are by weight and all solvent mixture proportions are by volume unless otherwise noted.

EXAMPLE 1

N-[3-(1-piperidinyl)propoxy]-pyridin-1-oxide-3-carboxamidine 1.86 g (0.033 mol) of KOH is dissolved in a mixture of 10 ml ethanol and 75 ml methanol. To the solution 4.59 g (0.03 mol) of nicotinamidoxime-1-oxide is added. After stirring for 15 minutes, a solution of 4.85 g (0.03 mol) of 1-chloro-3-(1-piperidinyl)-propane in 6 ml ethanol is added. The mixture is boiled for 12 hours, then the precipitate is filtered off, and the solution is evaporated. To the residue 30 ml of 2 N potassium carbonate solution is added, then extracted 3 times with 50 ml of chloroform. The organic phase is washed with 15 ml of 2 N potassium carbonate solution, dried over anhydrous magnesium sulfate, filtered and evaporated. The crude product is triturated with 40 ml tert.butyl-methyl-ether. This procedure is repeated, and the product obtained in the two steps is recrystallized in a 1:2 mixture of methanol and diethylether.

Yield: 1.72 g (21%).

$^1$H-NMR (methanol $d_4$): 8.62; 8.36; 7.82; 7.58; 4.22; 2.3-2.6; 1.92; 1.3-1.6.

$^{13}$C-NMR (methanol $d_4$: 149.4; 140.9; 138.0; 134.5; 127.9; 73.3; 57.4; 55.6; 27.4; 26.7; 25.4.

EXAMPLE 2

N-(3-(1-piperidinyl)propoxy]-pyridin-1-oxide-3-carboximidoyl chloride 1.668 g (6.0 mmol) of N-[3-(1-piperidinyl)-propoxy]-pyridin-1-oxide-3-carboxamidine is dissolved in a 1:1 mixture of cc. HCl and water, then at 0° C. added dropwise to a solution of 0.57 g (8.2 mmol) of $NaNO_2$ in 4 ml of water. The mixture is stirred for 2 hours at 0° C., then basified with 15 ml of 20% NaOH solution. It is then extracted three times with 15 ml of chloroform, the extract is dried over anhydrous sodium sulfate, filtered and evaporated. The residue is triturated with 15 ml of ether, filtered and dried. The precipitate is recrystallized from 6 ml of acetone.

Yield: 1.1 g (63%).

$^1$H-NMR (DMSO $d_6$): 8.56; 8.20; 7.98; 7.48; 2.4-2.6; 1.92; 1.45; 1.3.

$^{13}$C-NMR (DMSO $d_6$): 139.6; 136.7; 132.9; 132.3; 129.5 and 126.5; 73.6; 53.9; 52.9; 24.1; 23.5; 22.0.

EXAMPLE 3

N-[2-hydroxy-3-(1-piperidinyl)propoxy]-N'-n-butyl-pyridin-1-oxide-4-carboxamidine 1.18 g of N-[2-hydroxy-3-(1-piperidinyl)propoxy]-pyridin-1-oxide-4-carboximidoyl chloride is dissolved in a mixture of 18 ml of n-butylamine and 10 ml of 2-methoxyethyl-ether. The reaction mixture is heated under reflux for 24 hours. The n-butylamine is evaporated from the mixture, and to the residue 100 ml of 2 M potassium carbonate solution is added, then it is extracted 3 times with 10 ml of chloroform.

The extract is dried over anhydrous sodium sulfate, filtered and evaporated. The obtained material is recrystallized form ethylacetate.

Yield: 0.85 g (64%).

$^1$H-NMR (CDCl$_3$): 8.18; 7.36; 5.22; 4.06; 4.04; 2.97; 2.62 and 2.42; 1.2-1.7; 0.86.

$^{13}$C-NMR (CDCl$_3$): 153.1; 139.2; 129.2; 125.5; 76.4; 65.5; 60.8; 54.6; 43.9; 33.3; 25.6; 23.9; 19.6; 13.6.

EXAMPLE 4

N-[3-(1-oxido-1-piperidinyl)propoxy]-3-nitro-benzimidoyl-chloride dihydrate

To a solution of 1.0 g (3.0 mmol) of N-[3-(1-piperidinyl) propoxy]-3-nitro-benzimidoyl-chloride in 5 ml of chloroform a solution of 0.725 g (4.2 mmol) of m-chloroperbenzoic acid in 6 ml of chloroform is added. The reaction mixture is stirred for 6 hours at 25° C., then evaporated. To the residue 12 ml of 2 M potassium carbonate solution is added, and extracted 5 times with 20 ml of chloroform. The combined extracts are dried over magnesium sulfate, filtered and evaporated. The product is dissolved in ethanol; the solution is treated with charcoal then evaporated. The obtained material is triturated with ethylacetate, filtered and dried.

Yield: 0.74 g (63%).

$^1$H-NMR (CDCl$_3$): 8.62; 8.28; 8.18; 7.58; 4.52; 3.1-3.6; 2.2-2.6; 1.3-1.8.

$^{13}$C-NMR (CDCl$_3$): 148.2; 135.9; 134.0; 132.7; 129.6; 125.0; 122.0; 73.7; 67.0; 65.4; 22.4; 22.1; 20.9.

EXAMPLE 5

2-chloro-N-(3-(4-oxido-4-morpholinyl)propoxy-benzimidoyl chloride

Proceed according to Example 4, with the difference that as starting material 2-chloro-N-[3-(4-morpholinyl)-propoxy]-benzimidoyl chloride is used.

Yield: 82%.

EXAMPLE 6

(R,S)-5,6-dihydro-5-[(1-piperidinyl)methyl]-3-(1-oxido-3-pyridyl)-4H-1,2,4-oxadiazine a) 18.5 g (0.05 mol) of N-[2-hydroxy-3-(1-piperidinyl) propoxy]-pyridin-1-oxide-3-carboxamidine-hydrochloride is dissolved in 50 ml of thionylchloride, and the reaction mixture is heated under reflux for 1 hour. Next the reaction mixture is evaporated, the residue is dissolved in methanol, and the solution is treated with charcoal, filtered and evaporated. The residue is crystallized from a minimum quantity of ethanol. The yield of the obtained N-[2-chloro-3-(1-piperidinyl)propoxy]-pyridin-1-oxide-3-carboxamidine hydrochloride intermediate is 68%.

b) To a solution of 16.5 g (143.5 mmol) of potassium-tert.butylate in 150 ml of tert.butanol 11.8 g (34.1 mmol) N-[2-chloro-3-(1-piperidinyl)propoxy]-pyridin-1-oxide-3-carboxamidine hydrochloride intermediate is added. The reaction mixture is boiled for 5 hours, then evaporated. To the evaporation residue 100 ml of 5% NaOH solution is added, and the mixture is extracted 3 times with 300 ml of ethylacetate. The combined extracts are dried over sodium-sulfate, filtered and evaporated. The evaporation residue is triturated with ether, filtered, washed with ether and dried.

Yield: 34%.

Mp.: 154-158° C.

EXAMPLE 7

5,6-dihydro-5-[(4-benzyl-1-piperidinyl)methyl]-3-(3-pyridyl)-4H-1,2,4-oxadiazine Proceed according to Example 6, starting form the corresponding chlorinated amidine-compound.

Yield: 20%

Mp.: 178-180° C.

EXAMPLE 8

(R) or (S)-5,6-dihydro-5-[(2-oxo-1-piperidinyl)methyl]-3-(3-pyridyl)-4H-1,2,4-oxadiazine 2.5 g (9.6 mmol) of (−)-5,6-dihydro-5-(1-piperidinyl)-methyl-3-(3-pyridyl)-4H-1,2,4-oxadiazine is dissolved in 150 ml of 1% acetic acid, and to the solution 17.86 g (47.99 mmol) of ethylenediamine-tetraacetic acid disodium salt dihydrate, and 15.3 g (48 mmol) mercury(II)-acetate is added, and the reaction mixture is boiled for 2 hours while stirring. Then the reaction mixture is filtered, the filtrate is evaporated, to the residue 500 ml of methanol, and then in small portions 17.5 g (0.46 mol) sodium-[tetrahydrido-borate(III)] is added while stirring. After addition of the borohydride its excess is decomposed with 1:1 aqueous hydrochloric acid (pH=3), then the pH of the reaction mixture is set to 10 with 10% NaOH solution. The methanol is evaporated from the reaction mixture, and then the aqueous phase is extracted 3 times with 150 ml of chloroform. The combined chloroform phases are washed first with 100 ml of water, then with 50 ml of brine, the organic phase is dried over magnesium-sulfate, filtered and evaporated. The obtained oil (2 g) is purified by column chromatography (Kieselgel 60, eluent: 1:1 mixture of chloroform and methanol), and crystallized with a mixture of ethylacetate and ether (by the addition of very little amount of ethanol). 0.94 g (35.7%) pure material is obtained.

$^1$H-NMR: (CDCl$_3$): 8.9; 8.6; 7.92; 7.26; 6.68; 3.98; 3.96; 3.72-3.6; 3.42-3.22; 2.30; 1.76.

$^{13}$C-NMR (CDCl$_3$): 172.2; 150.8; 150.4; 146.9; 133.2; 128.6; 123.3; 65.1; 50.7; 50.5; 50.0; 32.1; 20.9.

EXAMPLE 9

(+)-5,6-dihydro-5-[(1-piperidinyl)methyl]-3-(1-oxido-3-pyridyl)-4H-1,2,4-oxadiazine 6.25 g (24 mmol) of (−)-5,6-dihydro-5-(1-piperidinyl)-methyl-3-(3-pyridyl)-4H-1,2,4-oxadiazine is dissolved in a mixture of 40 ml of water, 6.85 ml (120 mmol) of glacial acetic acid and 1.43 ml (24 mmol) of cc. H$_2$SO$_4$. The solution is heated to 60° C., and at this temperature 12 ml (75 mmol) of 21.5% hydrogen peroxide is added dropwise, and the reaction mixture is kept on stirring at this temperature. After 10 hours to the reaction mixture further 6 ml of 21.5% hydrogen peroxide is added dropwise. After another 20 hours the reaction mixture is cooled to 0° C., and it is introduced dropwise into 60 ml of 0° C. 20% NaOH, then extracted 5 times with 50 ml of dichloromethane. The combined organic phases are washed with water, dried over magnesium-sulfate and evaporated. The evaporation residue is purified by column chromatography. The suitable fractions are triturated with 20 ml of acetone and kept in refrigerator overnight. Next day the product is filtered, washed with cold acetone and dried, then recrystallized from ethanol-ethylacetate.

Yield: 13.7%.
Mp.: 165-168° C.

EXAMPLE 10

(R) or (S)-5,6-dihydro-5-[(1-oxido-1-piperidinyl)
methyl]-3-(1-oxido-3-pyridyl)-4H-1,2,4-oxadiazine Proceed according to Example 9. with the difference that the suitable column chromatographic fraction is isolated.
Yield: 3.4%.
$^1$H-NMR (D$_2$O): 8.38; 8.26; 7.76; 7.53; 4.6; 4.4; 3.9; 3.55-3.1; 1.95-1.25.
$^{13}$C-NMR (D$_2$O): 149.7; 139.9; 136.7; 131.6; 129.1; 126.9; 69.2; 65.6; 65.5; 44.3; 20.46; 20.30 and 20.17.

EXAMPLE 11

5,6-dihydro-5-[(4-hydroxy-1-piperidinyl)methyl]-3-(3-pyridyl)-4H-1,2,4-oxadiazine 20.55 g (150 mmol) of 3-pyridin-amidoxime and 20.1 g (360 mmol) of potassium hydroxide are dissolved in 95 ml of water and 28.5 ml of DMSO, then cooled to 0° C. At this temperature 20.85 g (17.7 ml, 225 mmol) of epichlorohydrine is added dropwise and the mixture is stirred for 3 hours. It is then extracted with 6×50 ml of ether, the combined organic phases are washed with 50 ml brine, dried over Na$_2$SO$_4$, treated with charcoal, filtered and evaporated.
m=6.08 g (21%)
The obtained evaporation residue is taken up in 90 ml of ether, the clear solution is decanted from the tar (1.18 g)—the ethereal solution contains 24.8 mmol epoxy compound—and to this solution 5.1 g (24.8 mmol) of 4-benzoyloxy-piperidine dissolved in 20 ml of iso-propanol is added. It is stirred at room temperature for 6 days, then the small amount of precipitate is filtered off, and the mother liquor is evaporated. The obtained 11.7 g of evaporation residue is taken up in 100 ml of water, extracted with 100 ml of ether, then 2×50 ml of ethylacetate, the organic phases are dried over Na$_2$SO$_4$ and evaporated.
m=8.77 g (88%)
Formation of monohydrochloride: 8.77 g of evaporation residue is dissolved in 44 ml iso-propanol (with slight heating), then 3.72 ml of 6M HCl/iPA is added. Upon heating the solution to boiling point, the separated gum dissolves. When it is then cooled back to room temperature, the monohydrochloride nicely precipitates. It is crystallized in a refrigerator for a few hours, then filtered off, and washed with cold iPA.
m=7.19 g (75.4%)
Mp.: 115-120° C.
Recrystallization: 7.19 g crude product form 150 ml of hot iso-propanol.
Crystallizes upon cooling.
m=5.87 mg (81.5%)
Mp.: 117-120° C.
5.87 g (13.5 mmol) of this monohydrochloride is suspended in 60 ml of dichloroethane, 30 ml of thionylchloride is added and is boiled for 1 hour. It is then cooled back to room temperature, 220 ml of methanol is added dropwise, treated with charcoal, filtered and evaporated. The obtained 7.5 g evaporation residue is triturated with 75 ml of ethylacetate, and crystallized by cooling. Filtered, washed with cold ethylacetate, then the wet precipitate is stirred with 50 ml of acetone.
The precipitate is filtered off, and washed with acetone.
m=5.76 g (87%)

5.76 g (11.75 mmol) of this "chloro-compound" is suspended in 120 ml of tert.butanol, 8.12 g (72.37 mmol) of potassium-tert.butylate is added and boiled for 1 hour. The precipitate is filtered and washed with a small amount of methanol, and the mother liquor is evaporated. The obtained 8.56 g of evaporation residue is taken up in 40 ml of water, extracted with 2×30 ml of chloroform, dried and evaporated. The residue (m=1.89 g) is triturated with 20 ml of ethylacetate, crystallized by cooling, filtered off, and washed with EtOAc.
m=1.19 g
Recrystallization: 1.19 mg of crude product from 13 ml of hot iso-propanol.
Crystallizes upon cooling.
m=605 mg
Mp.: 170-173° C.
$^1$H-NMR (the examined sample: PM-720-cs$_5$; solvent: CDCl$_3$+DMSO; reference: CDCl$_3$ MHz:300) [ppm]: 8.8 8.5 7.9 7.3 (m,4H,aromatic protons); 6.1 (m,1H,NH); 4.02 (m,1H,OCH$_2$); 3.74 (m,1H,CH); 3.62 (m,1H,CH—OH); 3.5 (m,1H,OCH$_2$); 2.9-2.3 (m,6H,3×CH$_2$N); 1.9-1.52 (m,4H,2× CH$_2$);
$^{13}$C-NMR (the examined sample: PM-720-cs$_5$; solvent: CDCl$_3$+DMSO; reference: CDCl$_3$ MHz:75.4) [ppm]: 150.4 (C=N); 150.9 146.9 133.5 128.6 123.3 (5C, Pyr-carbon atoms); 66.6 (OCH$_2$); 66.4 (CH—OH); 59.4 (CH$_2$N); 51.8 (CH$_2$N); 50.7 (CH$_2$N); 46.3 (CHN); 33.8 (2C, 2×CH$_2$).

EXAMPLE 12

N-[2-chloro-3-(1-piperidinyl)propoxy]-3-benzimidoyl-chloride hydrochloride 2.0 g of N-[2-hydroxy-3-(1-piperidinyl)propoxy]-benzimidoyl-chloride hydrochloride is dissolved in 10 ml of thionylchloride, then the solution is boiled for 2 hours. The thionylchloride is distilled off; the evaporation residue is taken up in 50 ml of methanol, then evaporated. The light yellow evaporation residue (m=2.48 g) is dissolved in 12.5 ml of ethanol and crystallized with 50 ml of ether. The separated precipitate is filtered off, and washed with a mixture of ethanol/ether.
m=1.68 g
Mp.: 154.5-1 58° C.
Recrystallization: by dissolving 320 mg in 1 ml warm MeOH, then precipitating with 3 ml of ether. The separated precipitate is filtered off and washed.
m=210 mg
Mp.: 155.5-160° C. (corr.)

EXAMPLE 13

N-[2-hydroxy-3-(1-piperidinyl)propoxy]-pyridin-1-oxide-3-carboxamide 4.0 g of N-[2-hydroxy-3-(1-piperidinyl)propoxy]-pyridin-1-oxide-3-carboximidoyl-chloride is stirred in 120 ml of 0.2 n NaOH at 60° C. for 5 days. The solution is neutralized with aqueous hydrochloric acid, evaporated, the residue is triturated with ethanol, and the obtained solution is evaporated again. The residue is crystallized with isopropanol, filtered off, and the obtained 1.0 g crude product is recrystallized from boiling isopropanol.
Yield: 0.8 g Mp.: 143-147° C.

EXAMPLE 14

Tablets

| | |
|---|---:|
| (+)-5,6-dihydro-5-[(1-piperidinyl)-methyl-3-(3-pyridyl)--4H-1,2,4-oxadiazine | 20.0 mg |
| corn starch | 100.0 mg |
| lactose | 95.0 mg |
| talc | 4.5 mg |
| magnesium stearate | 0.5 mg |

The active compound is finely ground, mixed with the excipients, the mixture is homogenized and granulated. The granulate is pressed into tablets.

EXAMPLE 15

Capsules

| | |
|---|---:|
| 5,6-dihydro-5-[(1-piperidinyl)-methyl-3-(3-pyridyl)--4H-1,2,4-oxadiazine | 20.0 mg |
| microcrystalline cellulose | 99.0 mg |
| amorphous silica | 1.0 mg |

The active ingredient is mixed with the additives, the mixture is homogenized and filled into gelatine capsules.

EXAMPLE 16

Dragées

| | |
|---|---:|
| N-[3-(1-oxido-1-piperidinyl)propoxy]-3-nitro-benzimidoyl-chloride dihydrate | 25.0 mg |
| lactose | 82.5 mg |
| potato starch | 33.0 mg |
| polyvinyl pyrrolidone | 4.0 mg |
| magnesium stearate | 0.5 mg |

The active ingredient and the polyvinyl pyrrolidone are dissolved in ethanol. The lactose and the potato starch are mixed, and the mixture is evenly wetted with the granulating solution of the active ingredient. After sieving, the wet granulate it is dried at 50° C. and sieved. Magnesium stearate is added and the granulate is pressed into dragée cores, which are then coated with sugar and polished with bee wax.

EXAMPLE 17

Suppositories

| | |
|---|---:|
| 5,6-dihydro-5-[(4-benzyl-1-piperidinyl)-methyl]-3-(3-pyridyl)--4H-1,2,4-oxadiazine | 4.0 mg |
| cocoa butter | 3.5 g |
| solid fat 50 suppository mass | 15.0 g |

The cocoa butter and the suppository mass are heated to 40° C., the active ingredient is dispersed in the melt, then the mass is cast into suppository forms.

EXAMPLE 18

Solution

| | |
|---|---:|
| 5,6-dihydro-5-[(4-hydroxy-1-piperidinyl)methyl]-3-(3-pyridyl)-4H-1,2,4-oxadiazine hydrochloride | 500 mg |
| sorbite | 10 g |
| saccharin sodium | 0.05 g |
| twice distilled water | q. s. ad 100 ml |

EXAMPLE 19

Injection

| | |
|---|---:|
| N-[2-chloro-3-(1-piperidinyl)propoxy]-3-benzimidoyl-chloride hydrochloride | 2 mg |
| physiological saline solution, pyrogen-free, sterile | q. s. ad 2.0 ml |

The solution is filled into 2 ml vials and the vials are sealed.

EXAMPLE 20

Infusion Solution

| Infusion solution of 500 ml volume is prepared with the following composition: | |
|---|---:|
| N-[2-hydroxy-3-(1-piperidinyl)propoxy]-pyridin-1-oxide-3-carboxamide methanesulfonate | 20 mg |
| physiological saline solution, pyrogen-free, sterile | q. s. ad 500 ml |

It should be understood that the examples and embodiments described herein are for illustrative purposes only and that various modifications or changes in light thereof will be suggested to persons skilled in the art and are to be included within the spirit and purview of this application.

We claim:

1. A method for treating a vascular disease or vascular disorder comprising administering to a patient in need thereof an effective amount of a compound of formula III as defined below:

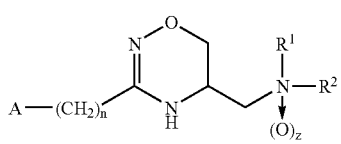

(III)

wherein $R^1$ and $R^2$ are independently hydrogen, straight chained $C_{1-6}$ alkyl group optionally substituted with a phenyl group, branched $C_{1-6}$ alkyl group optionally substituted with a phenyl group, or $R^1$ and $R^2$ together with the nitrogen atom attached thereto form a 5-7 membered saturated heterocyclic ring optionally containing further nitrogen and/or oxygen heteroatom, wherein said heterocyclic ring is optionally substituted with one or more hydroxy, oxo or benzyl groups;

A is a phenyl group optionally substituted with one or more $C_{1-4}$ alkyl, $C_{1-4}$ haloalkyl, nitro, or halogen, or is a 5-6 membered heteroaromatic ring containing at least one heteroatom is selected from the group consisting of nitrogen, oxygen and sulfur, wherein the nitrogen heteroatom is optionally an N-oxide structure;

n is 0, 1, or 2;

z is 0 or 1;

with the proviso that if $R^1$ and $R^2$ independently represent a hydrogen atom, a straight chained $C_{1-6}$ alkyl group optionally substituted with a phenyl group, a branched $C_{1-6}$ alkyl group optionally substituted with a phenyl group, or together with the nitrogen atom attached thereto form a 5-7 membered saturated heterocyclic ring optionally containing further nitrogen and/or oxygen heteroatom, then A is a heteroaromatic ring containing oxygen or sulfur heteroatom or an N-containing heteroaromatic ring having an N-oxide structure on the nitrogen heteroatom and if A is a phenyl group optionally substituted with one or more $C_{1-4}$ alkyl, $C_{1-4}$ haloalkyl or nitro groups or halogen, or is a 5-6 membered N-containing heteroaromatic ring, then $R^1$ and $R^2$ together with the nitrogen atom attached thereto form a 5-7 membered saturated heterocyclic ring optionally containing further nitrogen and/or oxygen heteroatom, wherein said heterocyclic ring is substituted with one or more hydroxy, oxo, or benzyl groups;

or a stereoisomer or salt thereof.

2. The method according to claim 1, wherein the compound is 5,6-dihydro-5-[(1-piperidinyl)methyl]-3-(1-oxido-3-pyridyl)-4H-1,2,4-oxadiazine, or a stereoisomer or salt thereof.

3. The method according to claim 1, wherein the compound is 5,6-dihydro-5-[(4-benzyl-1-piperidinyl)methyl]-3-(3-pyridyl)-4H-1,2,4-oxadiazine, or a stereoisomer or salt thereof.

4. The method according to claim 1, wherein the compound is 5,6-dihydro-5-[(2-oxo-1-piperidinyl)methyl]-3-(3-pyridyl)-4H-1,2,4-oxadiazine, or a stereoisomer or salt thereof.

5. The method according to claim 1, wherein the compound is (+)-5,6-dihydro-5-[(1-piperidinyl)methyl]-3-(1-oxido-3-pyridyl)-4H-1,2,4-oxadiazine, or a stereoisomer or salt thereof.

6. The method according to claim 1, wherein the compound is 5,6-dihydro-5-[(1-oxido-1-piperidinyl)methyl]-3-(1-oxido-3-pyridyl)-4H-1,2,4-oxadiazine, or a stereoisomer or salt thereof.

7. The method according to claim 1, wherein the compound is 5,6-dihydro-5-[(4-hydroxy-1-piperidinyl)methyl]-3-(3-pyridyl)-4H-1,2,4-oxadiazine, or a stereoisomer or salt thereof.

8. A method for inhibiting or reversing damage to one or more endothelial cells comprising administering to the one or more endothelial cells an effective amount of a compound of formula III as defined below:

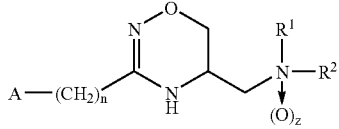

(III)

wherein $R^1$ and $R^2$ are independently hydrogen, straight chained $C_{1-6}$ alkyl group optionally substituted with a phenyl group, branched $C_{1-6}$ alkyl group optionally substituted with a phenyl group, or $R^1$ and $R^2$ together with the nitrogen atom attached thereto form a 5-7 membered saturated heterocyclic ring optionally containing further nitrogen and/or oxygen heteroatom, wherein said heterocyclic ring is optionally substituted with one or more hydroxy, oxo or benzyl groups;

A is a phenyl group optionally substituted with one or more $C_{1-4}$ alkyl, $C_{1-4}$ haloalkyl, nitro, or halogen, or is a 5-6 membered heteroaromatic ring containing at least one heteroatom is selected from the group consisting of nitrogen, oxygen and sulfur, wherein the nitrogen heteroatom is optionally an N-oxide structure;

n is 0, 1, or 2;

z is 0 or 1;

with the proviso that if $R^1$ and $R^2$ independently represent a hydrogen atom, a straight chained $C_{1-6}$ alkyl group optionally substituted with a phenyl group, a branched $C_{1-6}$ alkyl group optionally substituted with a phenyl group, or together with the nitrogen atom attached thereto form a 5-7 membered saturated heterocyclic ring optionally containing further nitrogen and/or oxygen heteroatom, then A is a heteroaromatic ring containing oxygen or sulfur heteroatom or an N-containing heteroaromatic ring having an N-oxide structure on the nitrogen heteroatom and if A is a phenyl group optionally substituted with one or more $C_{1-4}$ alkyl, $C_{1-4}$ haloalkyl or nitro groups or halogen, or is a 5-6 membered N-containing heteroaromatic ring, then $R^1$ and $R^2$ together with the nitrogen atom attached thereto form a 5-7 membered saturated heterocyclic ring optionally containing further nitrogen and/or oxygen heteroatom, wherein said heterocyclic ring is substituted with one or more hydroxy, oxo, or benzyl groups;

or a stereoisomer or salt thereof.

9. The method according to claim 8, wherein the compound is 5,6-dihydro-5-[(1-piperidinyl)methyl]-3-(1-oxido-3-pyridyl)-4H-1,2,4-oxadiazine, or a stereoisomer or salt thereof.

10. The method according to claim 8, wherein the compound is 5,6-dihydro-5-[(4-benzyl-1-piperidinyl)methyl]-3-(3-pyridyl)-4H-1,2,4-oxadiazine, or a stereoisomer or salt thereof.

11. The method according to claim 8, wherein the compound is 5,6-dihydro-5-[(2-oxo-1-piperidinyl)methyl]-3-(3-pyridyl)-4H-1,2,4-oxadiazine, or a stereoisomer or salt thereof.

12. The method according to claim 8, wherein the compound is (+)-5,6-dihydro-5-[(1-piperidinyl)methyl]-3-(1-oxido-3-pyridyl)-4H-1,2,4-oxadiazine, or a stereoisomer or salt thereof.

13. The method according to claim 8, wherein the compound is 5,6-dihydro-5-[(1-oxido-1-piperidinyl)methyl]-3-(1-oxido-3-pyridyl)-4H-1,2,4-oxadiazine, or a stereoisomer or salt thereof.

14. The method according to claim 8, wherein the compound is 5,6-dihydro-5-[(4-hydroxy-1-piperidinyl)methyl]-3-(3-pyridyl)-4H-1,2,4-oxadiazine, or a stereoisomer or salt thereof.

15. The method of claim 8, wherein the compound is administered to one or more of the endothelial cells in culture.

16. The method of claim 8, wherein the compound is administered to one or more endothelial cells of a patient.

17. A method for increasing vaso-relaxation of a vessel associated with endothelial cells comprising administering to the cells an effective amount of a compound of formula III as defined below:

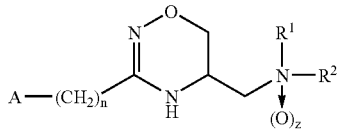

(III)

wherein R[1] and R[2] are independently hydrogen, straight chained $C_{1-6}$ alkyl group optionally substituted with a phenyl group, branched $C_{1-6}$ alkyl group optionally substituted with a phenyl group, or R[1] and R[2] together with the nitrogen atom attached thereto form a 5-7 membered saturated heterocyclic ring optionally containing further nitrogen and/or oxygen heteroatom, wherein said heterocyclic ring is optionally substituted with one or more hydroxy, oxo or benzyl groups;

A is a phenyl group optionally substituted with one or more $C_{1-4}$ alkyl, $C_{1-4}$ haloalkyl, nitro, or halogen, or is a 5-6 membered heteroaromatic ring containing at least one heteroatom is selected from the group consisting of nitrogen, oxygen and sulfur, wherein the nitrogen heteroatom is optionally an N-oxide structure;

n is 0, 1, or 2;

z is 0 or 1;

with the proviso that if R[1] and R[2] independently represent a hydrogen atom, a straight chained $C_{1-6}$ alkyl group optionally substituted with a phenyl group, a branched $C_{1-6}$ alkyl group optionally substituted with a phenyl group, or together with the nitrogen atom attached thereto form a 5-7 membered saturated heterocyclic ring optionally containing further nitrogen and/or oxygen heteroatom, then A is a heteroaromatic ring containing oxygen or sulfur heteroatom or an N-containing heteroaromatic ring having an N-oxide structure on the nitrogen heteroatom and if A is a phenyl group optionally substituted with one or more $C_{1-4}$ alkyl, $C_{1-4}$ haloalkyl or nitro groups or halogen, or is a 5-6 membered N-containing heteroaromatic ring, then R[1] and R[2] together with the nitrogen atom attached thereto form a 5-7 membered saturated heterocyclic ring optionally containing further nitrogen and/or oxygen heteroatom, wherein said heterocyclic ring is substituted with one or more hydroxy, oxo, or benzyl groups;

or a stereoisomer or salt thereof.

18. The method of claim 17, wherein the compound is administered to one or more of the endothelial cells in culture.

19. The method of claim 17, wherein the compound is administered to one or more endothelial cells of a patient.

* * * * *